(12) United States Patent
Wang et al.

(10) Patent No.: US 11,445,728 B2
(45) Date of Patent: Sep. 20, 2022

(54) APPLICATION METHOD OF SILICON QUANTUM DOTS FOR CONTROLLING CORN ARMYWORM

(71) Applicant: Jiangnan University, Wuxi (CN)

(72) Inventors: Zhenyu Wang, Wuxi (CN); Zhenggao Xiao, Wuxi (CN); Chuanxi Wang, Wuxi (CN); Le Yue, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/549,982

(22) Filed: Dec. 14, 2021

(65) Prior Publication Data
US 2022/0104499 A1 Apr. 7, 2022

Related U.S. Application Data

(63) Continuation of application No. PCT/CN2021/108891, filed on Jul. 28, 2021.

(30) Foreign Application Priority Data

Jan. 21, 2021 (CN) .......................... 202110100263.X

(51) Int. Cl.
*A01N 59/00* (2006.01)
*C09K 11/59* (2006.01)
*C01B 33/021* (2006.01)
*A01N 25/04* (2006.01)
*B82Y 20/00* (2011.01)
*B82Y 40/00* (2011.01)
*B82Y 5/00* (2011.01)

(52) U.S. Cl.
CPC ............. *A01N 59/00* (2013.01); *A01N 25/04* (2013.01); *C01B 33/021* (2013.01); *C09K 11/59* (2013.01); *B82Y 5/00* (2013.01); *B82Y 20/00* (2013.01); *B82Y 40/00* (2013.01); *C01P 2004/04* (2013.01); *C01P 2004/64* (2013.01); *C01P 2006/60* (2013.01)

(58) Field of Classification Search
CPC ...... A01N 59/00; A01N 25/04; C01B 33/021; C09K 11/59; B82Y 5/00; B82Y 20/00; B82Y 40/00; C01P 2004/04; C01P 2004/64; C01P 2006/60
See application file for complete search history.

(56) References Cited

FOREIGN PATENT DOCUMENTS

| CN | 1406482 A | 4/2003 |
|---|---|---|
| CN | 107156118 A | 9/2017 |
| CN | 109777401 A | 5/2019 |
| CN | 112841218 A | 5/2021 |

OTHER PUBLICATIONS

Rastogi et al., 3 Biotech (2019) 9:90, 1-11 (Year: 2019).*
Mousa,K.M. et. al, Growth Perturbation, abnormalities and mortality of oriental armyworm *Mythimna separata* (Walker) (Lepidoptera: Noctuidae) caused by silica nanoparticles and bacillus thuringiensis toxin, Egyptian journal of biological pest control, Jan. 31, 2014, V2, Issue 24, 347-351.

* cited by examiner

*Primary Examiner* — Robert S Cabral
(74) *Attorney, Agent, or Firm* — IPro, PLLC; Na Xu

(57) ABSTRACT

The present disclosure discloses an application method of silicon quantum dots (Si QDs) for controlling corn armyworm, belonging to the technical field of nano-agricultural technology for crop pest control. The method for controlling corn armyworm by using Si QDs of the present disclosure includes the following steps of: preparing the Si QDs into an aqueous solution of the Si QDs, and then applying the aqueous solution on the roots or leaves of plants as plant fertilizer; where the concentration of the aqueous solution of the Si QDs is 10-150 mg/L; the size of the Si QDs is 3-8 nm. The method of the present disclosure not only improves the effect of the conventional silicon fertilizer on the stress resistance of plants, but also directly improves the direct insecticidal effect of the nano-silicon and improves the chemical defense capability of plants; the optimal spraying amount of Si QDs is determined by spraying different concentrations of Si QDs in the growth and development experiment of armyworm.

10 Claims, 1 Drawing Sheet

APPLICATION METHOD OF SILICON QUANTUM DOTS FOR CONTROLLING CORN ARMYWORM

TECHNICAL FIELD

The present disclosure herein relates to an application method of silicon quantum dots for controlling corn armyworm, belonging to the technical field of nano-agricultural technology for crop pest control.

BACKGROUND

*Mythimna separata*, belonging to Lepidoptera Noctuidae, is a typical seasonal long-distance migratory pest. It is also a major pest on food crops in China and other Asian and Australian countries. It has the characteristics of wide occurrence range, many generations of hazards, many kinds and organizations of damaged crops, heavy yield loss and long occurrence history of damage. At present, chemical pesticides are still the main means of controlling armyworm in China, but the negative effects of unscientific application of traditional pesticides on the ecological environment, human health and biodiversity are becoming increasingly prominent. For example, the extensive use of chemical pesticides has caused serious pollution to the air, soil and water body, led to the death of non-target organisms, continued increase of drug resistance of pests, and excessive pesticide residues threatening food safety and so on. Therefore, it is of great significance for the green control of armyworm to develop high activity and environmentally-friendly pest control measures.

Silicon, its content in the earth's crust is second after oxygen, is a relatively inert and environmentally-friendly plant beneficial element. Particularly, it plays an important role in improving the resistance of plants to a series of abiotic (drought, salt, heavy metal, low temperature and the like) and biotic (pest) stresses. At present, the slowly released soluble silicon in a large amount of farmland soils in China can no longer meet the silicon demand of crops (e.g., rice, corn and other silicophilic plants), which has seriously restricted the high and stable yield of farmland crops. In order to improve crop yield and resistance against stress, the amount of traditional silicate fertilizer is continuously increased in agricultural production, which further aggravates the soil hardening, soil structure destruction and fertility decline.

In 1959, physicist Richard Feynman proposed the concept of nanotechnology, which attracted the attention of experts and scholars all over the world. Nanotechnology is widely used in many fields. Among them, nano-pesticide is one of the directions for the effective application of nanotechnology in agriculture. Compared with conventional pesticides, nano-pesticides have larger surface area and biocompatibility, making them have significant advantages in the efficient control of agricultural pests. The results showed that the nano-silver modified by polyvinylpyrrolidone can effectively inhibit the growth of larvae and pupae of Lepidoptera pest *Spodoptera litura*. Nickel nanoparticles can effectively kill 93% of adult bean beetles. Although metal nanoparticles have a high insecticidal effect, the release of large doses of metal-based nanoparticles (e.g., nano-silver and nano-copper) into the environment will also lead to the toxicity of heavy metals, and eventually cause the risk of environmental pollution.

SUMMARY

In order to solve at least one of the above problems, the present disclosure applies silicon quantum dots (Si QDs) to the control of corn armyworm and establishes an optimal control system of corn armyworm. The application process of the present disclosure is simple and easy to operate.

The first objective of the present disclosure is to provide an application method of Si QDs for controlling corn armyworm, which includes the following steps of: preparing the Si QDs into an aqueous solution of the Si QDs, and then applying the aqueous solution to the roots or leaves of plants as plant fertilizer.

In one example of the present disclosure, the concentration of the aqueous solution of the Si QDs is 10-150 mg/L.

In one example of the present disclosure, the size of the Si QDs is 3-8 nm.

In one example of the present disclosure, the concentration of the aqueous solution of Si QDs applied to the roots is 50 mg/L; the volume of the aqueous solution of Si QDs sprayed on the roots is 200 mL/plant.

In one example of the present disclosure, the concentration of the aqueous solution of the Si QDs sprayed on a leaf surface is 50-150 mg/L; the volume of the aqueous solution of the Si QDs sprayed on the leaf surface was 20 mL/plant.

In one example of the present disclosure, the period of application is a three-leaf and one-heart stage of the plant.

In one example of the present disclosure, the plant is corn.

In one example of the present disclosure, the preparation method of the Si QDs is as follows.

N-aminoethyl-3-aminopropylmethyl dimethoxysilane, ascorbic acid and water are weighed and uniformly mixed, and then reacted in a water bath at 70-90° C. for 7-10 hours. After the reaction is completed, dialysis, centrifugation and dry is performed to obtain the Si QDs.

In one example of the present disclosure, the ratio of N-aminoethyl-3-aminopropylmethyl dimethoxysilane, ascorbic acid and water in the preparation method of the Si QDs is 1-3 mL: 2-3 g: 7-9 mL.

In one example of the present disclosure, the reaction process in the preparation method of the Si QDs needs continuous stirring.

In one example of the present disclosure, in the preparation method of the Si QDs, the dialysis is performed by using a dialysis bag (1 kDa, molecular weight cut-off), to remove excess reactants.

In one example of the present disclosure, in the preparation method of the Si QDs, the centrifugation is performed at 4° C. and 10000 r/min for 20 min.

The present disclosure has the beneficial effects that:

(1) after the silicon is subjected to nanocrystallization, the present disclosure not only improves the effect of the conventional silicon fertilizer on the stress resistance of plants, but also directly improves the direct insecticidal effect of the nano-silicon and improves the chemical defense capability of plants. The optimal spraying amount of the Si QDs is determined through the growth and development experiment of spraying the Si QDs with different concentrations on the armyworm, and compared with the traditional pesticide control method, the control method of can effectively avoid the accidental killing of non-target insects and environmental pollution.

(2) the Si QDs adopted by the present disclosure can be used as exogenous abiotic elicitors of plant to induce the metabolism and synthesis of the plant insect-resistant phenolic substance, improve the content of total phenolics and chlorogenic acid of the insect-resistant substances in the leaves and further inhibit the invasion and growth of armyworm.

(3) in the present disclosure, the Si QDs are applied on the corn plants, so that the content of insect-resistant substances chlorogenic acid in the corn leaves is remarkably improved to be 33.3% and above and can be up to 70.3%; the content of the total phenolics in the corn leaves is increased, and can reach 53.5% and above; growth of the armyworm is inhibited to be 21.8% and above; and net photosynthesis of the corn leaves is increased by up to 38.6%, and the biomass of aboveground part of the corn is increased by 40%.

DETAILED DESCRIPTION

Figure 1:
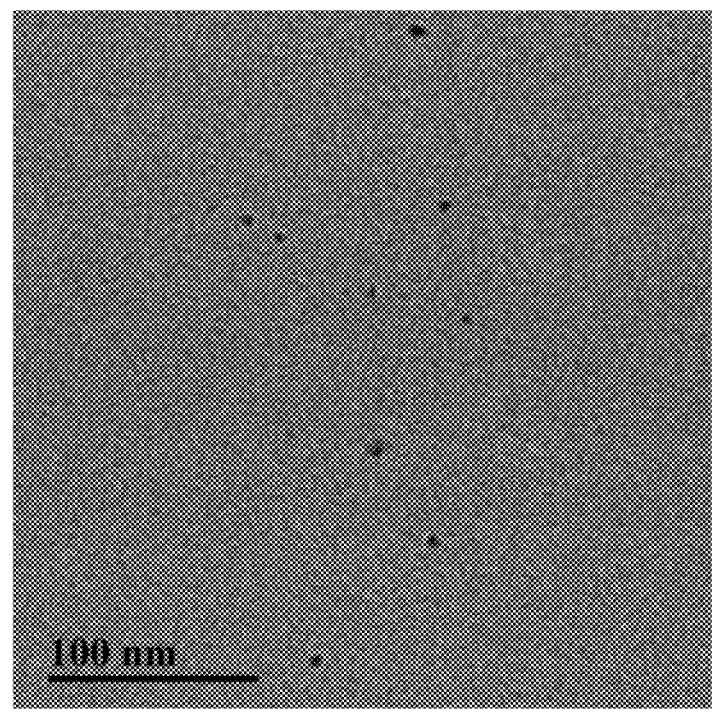
FIG. 1 is a TEM photograph of the prepared Si QDs.

The preferred examples of the present disclosure will be described below. It should be understood that the examples are for better explanation of the present disclosure and are not used to limit the present disclosure.

Test Method:

TEM characterization: the size and morphology of the prepared Si QDs with different particle sizes were characterized by JEM-2100 transmission electron microscope.

FT-IR characterization: the surface functional groups of the Si QDs were analyzed by Fourier transform infrared (FTIR) spectroscopy.

Determination of chlorogenic acid content: The chlorogenic acid in leaves was determined by high performance liquid chromatography (HPLC). 100 mg of fresh leaf tissue was ground in liquid nitrogen, and 2 mL of 70% methanol (v/v) was added, and placed in an ultrasonic water bath for 50 minutes. The solution was then centrifuged at 10000 rpm for 5 minutes, and the supernatant was collected and diluted to 10 mL. The extracts were then filtered over a 0.22 μm membrane and analyzed by an HPLC system (Agilent Technologies Inc., USA) using an Eclipse Plus C18 column (5 μm, 4.6×250 mm) at 30° C. Liquid phase conditions: solvent A (acetonitrile) and solvent B (0.1% formic acid) were used to form a mobile phase: 0-5 minutes (10-15% A), 5-10 minutes (15-20% A), and 10-15 minutes (20-10% A). The flow rate was maintained at 0.5 mL/min. The detection wavelength was set to 280 nm and the injection volume was 5 μL.

Determination of total phenolics: Folin-Ciocalteu colorimetric method was used: 20 mg of leaf tissue was ground into a homogeneous powder in liquid nitrogen and extracted with 2 mL of pre-cooled 95% (v/v) methanol for 48 hours at room temperature. Then, 200 mL of 10% (v/v) Folin-Ciocalteu reagent was mixed with 100 mL of the extracts, the standard substance (gallic acid), and 95% (v/v) of methanol blank solution, respectively. 800 mL of 700 mM $Na_2CO_3$ solution was added and incubated at room temperature for 2 hours to determine absorbance thereof at 765 nm.

The test method of shoot biomass: the base of corn plant stem was cut, and then the mass of the aboveground plant tissue was determined by using an electronic balance.

Test of net photosynthetic rate: The penultimate leaf of corn plant was selected, and its net photosynthetic rate was determined by photosynthetic apparatus (CIRAS-3, PP-Systems, USA).

Test of armyworm larval weight gain: =larvae weight of armyworm post 48 h inoculation—larvae weight before inoculation.

Example 1

A preparation method of a Si QDs, which includes the following steps:

2.3 g ascorbic acid was weighed and dissolved in 8.0 mL of water, and 2.0 mL of N-aminoethyl-3-aminopropylmethyl dimethoxysilane was added and mixed uniformly at 80° C. The mixture was stirred for 8 h in a water bath at 80° C. for reaction. After the reaction is completed, excess reactants were removed using a dialysis bag (1 kDa, molecular weight cut-off); then the solution after dialysis was centrifuged at 4° C. at 10000 r/min for 20 min; precipitate was dried to obtain the Si QDs.

Figure 2:
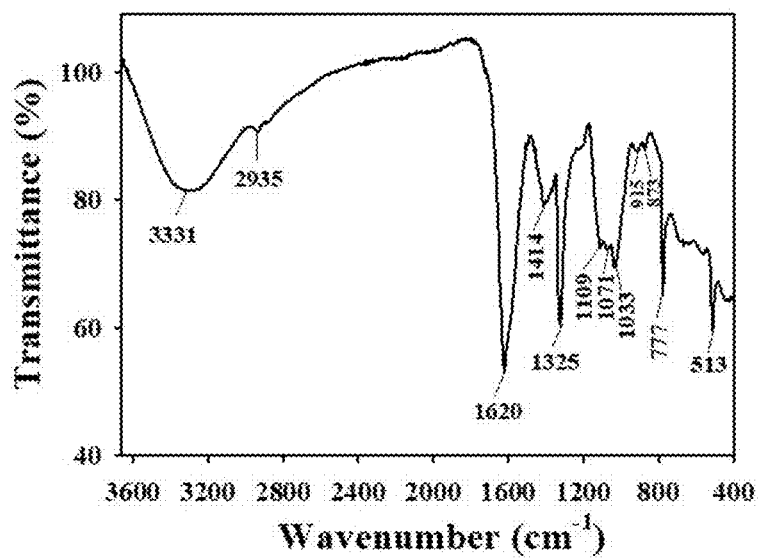
FIG. 2 is a FT-IR photograph of the prepared Si QDs.

The size of obtained Si QDs is around 5 nm, determined by TEM (as shown in FIG. 1), and there is functional groups such as —OH and —NH on the surface of the Si QDs (as shown in FIG. 2), the hydration diameter and zeta potential of Si QDs is about 42.9 nm and 10.6 eV, respectively.

Example 2

An application method of Si QDs for controlling corn armyworm, which includes the following steps:

(1) Corn seeds (Su Yu 29) from Jiangsu Academy of Agricultural Sciences were disinfected in a 5% sodium hypochlorite solution for 10 minutes and then rinsed 3 times with deionized water for disinfection;

(2) after disinfection was completed, the corn seeds were soaked in deionized water for 4 hours, and then the corn seeds were placed into a culture dish padded with damp filter paper, cultured under a dark condition in a greenhouse, and water was sprayed regularly every day;

(3) after culture for 5 days, the corn seeds with uniform sprouting were selected and transferred into a basin filled with 1.0 Kg soil for growth;

(4) when the corn seedlings grew to have three leaves and one heart, 20 mL of the aqueous solution of Si QDs (Example 1) with a concentration of 50 mg/L was sprayed on the leaves; the corn seedlings were inoculated with the same amount (3 individuals) of third instar armyworm larvae (Keyun Biology), and the growth and development of the armyworm were evaluated after 48 hours of infection.

Test result: The growth (body weight) of armyworm was inhibited by 35.1% after 48 hours of Si QDs application (Table 1)

Example 3

The concentration of the aqueous solution of Si QDs (Example 1) in Example 2 was adjusted to 10 mg/L and 150 mg/L, and the rest was the same as that in Example 2.

Comparative Example 1

The aqueous solution of Si QDs in Example 2 was adjusted to the water, and the rest was the same as that in Example 2.

Comparative Example 2

The aqueous solution of Si QDs in Examples 2 and 3 was adjusted to the aqueous solution of traditional silicon fertilizer sodium silicate, and the rest was the same as that in Example 2.

The test results of Examples 2 and 3 and Comparative Examples 1 and 2 were as follows.

TABLE 1

Test results of Examples 2 and 3 and Comparative Examples 1 and 2

| Example | Concentration (mg/L) | Content of chlorogenic acid (mg/g) | Content of total phenolics (mg/g) | 48 h larval weight gain (mg) | Shoot biomass (g) | Net photosynthesis ($\mu mol\ CO_2\ m^{-2}\ S^{-1}$) |
|---|---|---|---|---|---|---|
| Example 2 | 50 | 0.46 ± 0.04 | 30.4 ± 4.3 | 31.8 ± 5.0 | 4.2 ± 0.4 | 19.0 ± 2.0 |
| Example 3 | 10 | 0.38 ± 0.04 | 21.4 ± 3.1 | 35.6 ± 3.7 | 3.5 ± 0.4 | 15.6 ± 2.2 |
|  | 150 | 0.36 ± 0.03 | 18.7 ± 2.7 | 38.3 ± 3.6 | 3.8 ± 0.3 | 17.5 ± 2.4 |
| Comparative Example 1 | 0 | 0.27 ± 0.06 | 19.8 ± 3.5 | 49.0 ± 5.2 | 3.0 ± 0.3 | 13.7 ± 2.4 |
| Comparative Example 2 | 10 | 0.30 ± 0.06 | 20.1 ± 3.4 | 40.1 ± 2.9 | 3.1 ± 0.3 | 15.0 ± 2.5 |
|  | 50 | 0.35 ± 0.04 | 21.6 ± 2.1 | 36.8 ± 3.0 | 3.7 ± 0.4 | 15.9 ± 1.8 |
|  | 150 | 0.32 ± 0.05 | 23.5 ± 3.9 | 41.1 ± 3.7 | 3.8 ± 0.3 | 16.1 ± 2.1 |

Leaf spraying of 10, 50 and 150 mg/L of the aqueous solution of Si QDs significantly increased the content of insect-resistant substance chlorogenic acid in corn leaves by 40.7%, 70.3% and 33.3%, respectively, while leaf spraying of 10, 50 and 150 mg/L conventional silicon fertilizer sodium silicate increased the content of chlorogenic acid in leaves by 11.1%, 29.6% and 18.5%, respectively (Table 1). In addition, spraying of 50 mg/L Si QDs aqueous solution and conventional silicon fertilizer sodium silicate also increased the content of insect-resistant substance total phenolics in corn leaves by 53.5% and 9.0% respectively (Table 1).

After leaf spraying 10, 50 and 150 mg/L Si QDs aqueous solution for 48 hours, the growth of armyworm was inhibited by 27.3%, 35.1% and 21.8%, respectively (Table 1), while the growth of armyworm was inhibited by 18.1%, 24.8% and 16.1% with 10, 50 and 150 mg/L conventional silicon fertilizer sodium silicate (Table 1). Si QDs can improve the net photosynthesis of corn leaves, especially when spraying 50 mg/L Si QDs increased the net photosynthesis of corn leaves by 38.6%, and finally increased the shoot biomass by 40% (Table 1).

Therefore, leaf spraying 50 mg/L of Si QDs on has the best control effect on armyworm, and effectively alleviates the harm of armyworm to corn and promotes the growth of corn.

Comparative Example 3

The aqueous solution of Si QDs in Example 2 was adjusted to spray 5 nm nano-silica solution, and the rest was the same as that in Example 2.

The test results of Example 2 and Comparative Example 3 were as follows.

The promotion effect of Si QDs on the contents of chlorogenic acid and total phenolics in corn leaves as well as on net photosynthesis and biomass was significantly superior to that of nano-silica treatment with equivalent concentration (Table 2).

TABLE 2

Test results of Comparative Example 3

| Example | Concentration (mg/L) | Content of chlorogenic acid (mg/g) | Content of total phenolics (mg/g) | 48 h larval weight gain (mg) | Shoot biomass (g) | Net photosynthesis ($\mu mol\ CO_2\ m^{-2}\ S^{-1}$) |
|---|---|---|---|---|---|---|
| Example 2 | 50 | 0.46 ± 0.04 | 30.4 ± 4.3 | 31.8 ± 5.0 | 4.2 ± 0.4 | 19.0 ± 2.0 |
| Comparative Example 3 | 50 | 0.35 ± 0.05 | 22.0 ± 3.2 | 36.9 ± 3.6 | 3.6 ± 0.3 | 15.8 ± 1.4 |

Example 4

The particle size of the Si QDs in example 2 was adjusted as shown in Table 3, and the rest was the same as that in example 2.

The test results of Example 2 and Example 4 were as follows.

Si QDs with different particle sizes have no obvious difference in promoting the insect resistance and growth of corn, among which the 5 nm Si QDs have the best promotion effects on the content of insect-resistant substances and growth of corn (Table 3).

TABLE 3

Test results of Example 4

| Particle size (nm) | Content of chlorogenic acid (mg/g) | Content of total phenolics (mg/g) | 48 h larval weight gain (mg) | Shoot biomass (g) | Net photosynthesis ($\mu mol\ CO_2\ m^{-2}\ S^{-1}$) |
|---|---|---|---|---|---|
| 5 (Example 2) | 0.46 ± 0.04 | 30.4 ± 4.3 | 31.8 ± 5.0 | 4.2 ± 0.4 | 19.0 ± 2.0 |
| 8 | 0.40 ± 0.05 | 27.0 ± 4.4 | 36.3 ± 3.2 | 4.0 ± 0.3 | 18.8 ± 1.2 |
| 3 | 0.39 ± 0.04 | 26.2 ± 2.5 | 35.7 ± 3.0 | 3.9 ± 0.3 | 18.6 ± 1.3 |

Example 5

The foliar application mode of Example 2 was adjusted to the soil application of the aqueous solution of Si QDs (Example 1). The specific steps were as follows.

(1) Corn seeds (Su Yu 29) from Jiangsu Academy of Agricultural Sciences (China) were disinfected in a 5% sodium hypochlorite solution for 10 minutes and then rinsed 3 times with deionized water for disinfection;

(2) after disinfection was completed, the corn seeds were soaked in deionized water for 4 hours, and then the corn seeds were placed into a culture dish padded with damp filter paper, cultured under a dark condition in a greenhouse, and water was sprayed regularly every day;

(3) after culture for 5 days, the corn seeds with uniform sprouting were selected and transferred into a basin filled with 1.0 Kg soil for growth, subsequently, 200 mL of aqueous solution of a 50 mg/L of Si QDs (Example 1) was applied to the soil; when the corn seedlings grew to have three leaves and one heart, the corn seedlings were inoculated with the same amount (3 individuals) of third instar armyworm larvae (Keyun Biology), and the growth and development of the armyworm were evaluated after 48 hours of infection.

The test results of Example 2 and Example 5 were as follows.

Compared with spraying the Si QDs solution on the leaf surface, the total phenolics content of corn was increased by 16.1% by applying the Si QDs to the soil, and finally the inhibition effect on the growth (body weight) of armyworm was more obvious (Table 4).

TABLE 4

Test results of Example 5

| Example | Mode of application | Content of chlorogenic acid (mg/g) | Content of total phenolics (mg/g) | 48 h larval weight gain (mg) | Shoot biomass (g) | Net photosynthesis ($\mu mol\ CO_2\ m^{-2}\ S^{-1}$) |
|---|---|---|---|---|---|---|
| Example 2 | Foliage application | 0.46 ± 0.04 | 30.4 ± 4.3 | 31.8 ± 5.0 | 4.2 ± 0.4 | 19.0 ± 2.0 |
| Example 5 | Soil application | 0.49 ± 0.07 | 35.3 ± 3.4 | 26.7 ± 2.9 | 4.4 ± 0.6 | 20.6 ± 2.5 |

Although the present disclosure has been disclosed as a preferred example, it is not intended to limit the present disclosure. Anyone familiar with this technology can make various changes and modifications without departing from the spirit and scope of the present disclosure, so the scope of protection of the present disclosure should be defined by the claims.

What is claimed is:

1. A method comprising:
   preparing silicon quantum dots (Si QDs) by obtaining a mixture of N-aminoethyl-3-aminopropylmethyl dimethoxysilane, ascorbic acid and water, maintaining the mixture at 70-90° C. for 7-10 hours, and dialyzing, centrifuging and drying the mixture;
   preparing an aqueous solution of the Si QDs, and applying the aqueous solution to a plant;
   wherein the concentration of the aqueous solution of the Si QDs is 10-150 mg/L.

2. The method of claim 1, wherein the size of the Si QDs is 3-8 nm.

3. The method of claim 1, wherein the concentration of the aqueous solution is 50 mg/L and 200 mL of the aqueous solution is applied to roots of the plant.

4. The method of claim 1, wherein the concentration of the aqueous solution is 50-150 mg/L and 20 mL of the aqueous solution is applied to leaves of the plant.

5. The method of claim 1, wherein the aqueous solution is applied to the plant when the plant is at a three-leaf and one-heart stage.

6. The method of claim 1, wherein the plant is corn.

7. The method of claim 1, wherein the plant is infested by armyworms.

8. The method of claim 1, wherein the ratio of N-aminoethyl-3-aminopropylmethyl dimethoxysilane, ascorbic acid and water is 1-3 ml: 2-3 g: 7-9 mL.

9. The method of claim 1, wherein centrifuging is performed at 4° C. at 10000 r/min for 20 min.

10. The method of claim 1, wherein the mixture is continuously stirred.

* * * * *